(12) United States Patent
Crump et al.

(10) Patent No.: US 7,021,313 B1
(45) Date of Patent: Apr. 4, 2006

(54) RESPIRATORY SUCTION CATHETER APPARATUS WITH IMPROVED VALVE AND COLLAR

(75) Inventors: Chet M. Crump, Draper, UT (US); Edward B. Madsen, Riverton, UT (US)

(73) Assignee: Ballard Medical Products, Draper, UT (US)

(*) Notice: Subject to any disclaimer, the term of this patent is extended or adjusted under 35 U.S.C. 154(b) by 715 days.

(21) Appl. No.: 09/716,486

(22) Filed: Nov. 20, 2000

Related U.S. Application Data (63) Continuation of application No. 09/157,605, filed on Sep. 21, 1998, now abandoned.

(51) Int. Cl.
*A61M 16/00* (2006.01)
*A61M 1/00* (2006.01)

(52) U.S. Cl. .......................... 128/207.14; 128/207.16; 604/30

(58) Field of Classification Search ........... 128/207.14, 128/207.16, 207.15, 200.26; 604/30, 171, 604/164.02, 246, 256, 537, 19, 264
See application file for complete search history.

(56) References Cited

U.S. PATENT DOCUMENTS

| | | | |
|---|---|---|---|
| 3,240,431 A | 3/1966 | Hug et al. | |
| 3,710,942 A * | 1/1973 | Rosenberg | ................. 210/136 |
| 3,831,629 A | 8/1974 | Mackal et al. | |
| 3,834,388 A | 9/1974 | Sauer | |
| 3,902,500 A | 9/1975 | Dryden | |
| 3,937,220 A | 2/1976 | Coyne | |
| 3,991,762 A | 11/1976 | Radford | |
| 4,015,336 A | 4/1977 | Johnson | |
| 4,047,527 A | 9/1977 | Kelsen | |
| 4,193,406 A | 3/1980 | Jinotti | |
| 4,351,328 A | 9/1982 | Bodai | |
| 4,468,224 A | 8/1984 | Enzmann et al. | |
| 4,510,933 A | 4/1985 | Wendt et al. | |
| 4,516,573 A | 5/1985 | Gedeon | |
| 4,529,003 A * | 7/1985 | Iannuzzelli et al. | ...... 137/493.8 |
| 4,569,344 A | 2/1986 | Palmer | |
| 4,573,965 A | 3/1986 | Russo | |
| 4,573,979 A | 3/1986 | Blake | |
| 4,574,173 A | 3/1986 | Bennett | |
| 4,595,005 A | 6/1986 | Jinotti | |
| 4,622,964 A * | 11/1986 | Flynn | .................... 128/205.24 |
| 4,638,539 A | 1/1987 | Palmer | |
| 4,649,913 A | 3/1987 | Watson | |
| 4,657,008 A | 4/1987 | Broddner et al. | |
| 4,691,702 A * | 9/1987 | Chantzis | ................. 128/207.16 |
| 4,696,305 A | 9/1987 | von Berg | |
| 4,705,073 A | 11/1987 | Beck | |
| 4,834,726 A | 5/1989 | Lambert | |

(Continued)

OTHER PUBLICATIONS

Hudson RCI advertisement for "Cath-Guide", 1996.

(Continued)

*Primary Examiner*—Teena Mitchell
(74) *Attorney, Agent, or Firm*—Dority & Manning (57) ABSTRACT

An improved respiratory suction apparatus catheter includes a manifold for attachment to the distal hub of an endotracheal tube to form a respiration circuit, a catheter tube which is displaceable through the manifold and into the endotracheal tube to suction secretions from the tube and lungs, and a valve mechanism disposed adjacent the respiration circuit to minimize the draw of air from the respiration circuit of a patient while the catheter tube is being cleaned. In a preferred embodiment of the invention, the catheter tube is cleaned more thoroughly than in the prior art while simultaneously drawing little or no air from the patient's respiration circuit.

12 Claims, 9 Drawing Sheets

U.S. PATENT DOCUMENTS

| | | | |
|---|---|---|---|
| 4,909,248 A | 3/1990 | McLennan Anderson | |
| 4,929,426 A | 5/1990 | Bodai et al. | |
| 4,967,743 A | 11/1990 | Lambert | |
| D312,880 S | 12/1990 | Bodai et al. | |
| 5,005,568 A * | 4/1991 | Loescher et al. | 128/202.28 |
| 5,060,646 A | 10/1991 | Page | |
| 5,064,122 A | 11/1991 | Kamishita et al. | |
| 5,073,164 A | 12/1991 | Hollister et al. | |
| 5,083,561 A | 1/1992 | Russo | |
| 5,088,486 A | 2/1992 | Jinotti | |
| 5,107,829 A | 4/1992 | Lambert | |
| 5,125,893 A | 6/1992 | Dryden | |
| 5,134,996 A | 8/1992 | Bell | |
| 5,139,018 A | 8/1992 | Brodsky et al. | |
| 5,140,983 A | 8/1992 | Jinotti | |
| 5,158,569 A | 10/1992 | Strickland et al. | |
| 5,184,611 A | 2/1993 | Turnbull | |
| 5,191,881 A | 3/1993 | Beck | |
| 5,213,096 A | 5/1993 | Kihlberg et al. | |
| 5,215,522 A | 6/1993 | Page et al. | |
| 5,224,471 A | 7/1993 | Marelli et al. | |
| 5,230,332 A | 7/1993 | Strickland | |
| 5,242,084 A | 9/1993 | Jinotti | |
| 5,254,098 A | 10/1993 | Ulrich et al. | |
| 5,255,676 A | 10/1993 | Russo | |
| 5,277,177 A | 1/1994 | Page et al. | |
| 5,300,043 A | 4/1994 | Devlin et al. | |
| 5,305,762 A | 4/1994 | Acorn et al. | |
| 5,309,902 A | 5/1994 | Kee et al. | |
| 5,309,904 A | 5/1994 | Beck | |
| 5,325,850 A | 7/1994 | Ulrich et al. | |
| 5,325,851 A | 7/1994 | Reynolds et al. | |
| 5,333,606 A | 8/1994 | Schneider et al. | |
| 5,333,607 A | 8/1994 | Kee et al. | |
| 5,337,780 A | 8/1994 | Kee | |
| 5,343,857 A | 9/1994 | Schneider et al. | |
| 5,346,478 A | 9/1994 | Jinotti | |
| 5,348,542 A * | 9/1994 | Ellis | 604/173 |
| 5,349,950 A | 9/1994 | Ulrich et al. | |
| 5,354,267 A * | 10/1994 | Niermann et al. | 604/32 |
| 5,355,876 A | 10/1994 | Brodsky et al. | |
| 5,357,946 A | 10/1994 | Kee et al. | |
| 5,368,017 A | 11/1994 | Sorenson et al. | |
| 5,370,610 A * | 12/1994 | Reynolds | 604/43 |
| 5,385,560 A * | 1/1995 | Wulf | 604/264 |
| 5,445,141 A | 8/1995 | Kee et al. | |
| 5,449,348 A | 9/1995 | Dryden | |
| 5,460,613 A | 10/1995 | Ulrich et al. | |
| 5,487,381 A | 1/1996 | Jinotti | |
| 5,490,503 A | 2/1996 | Hollister | |
| 5,496,287 A | 3/1996 | Jinotti | |
| 5,513,627 A | 5/1996 | Flam | |
| 5,513,628 A | 5/1996 | Coles et al. | |
| 5,578,006 A | 11/1996 | Schön | |
| 5,582,161 A | 12/1996 | Kee | |
| 5,582,165 A | 12/1996 | Bryan et al. | |
| 5,598,840 A | 2/1997 | Iund et al. | |
| 5,605,149 A | 2/1997 | Warters | |
| 5,613,663 A * | 3/1997 | Schmidt et al. | 251/149.2 |
| 5,628,306 A | 5/1997 | Kee | |
| 5,642,726 A | 7/1997 | Owens et al. | |
| 5,664,594 A | 9/1997 | Kee | |
| 5,676,136 A | 10/1997 | Russo | |
| 5,715,815 A * | 2/1998 | Lorenzen et al. | 128/207.14 |
| 5,730,123 A * | 3/1998 | Lorenzen et al. | 128/207.14 |
| 5,735,271 A * | 4/1998 | Lorenzen et al. | 128/207.16 |
| 5,738,091 A * | 4/1998 | Kee et al. | 128/205.12 |
| 5,769,093 A * | 6/1998 | Bays | 128/898 |
| 5,769,702 A | 6/1998 | Hanson | |
| 5,775,325 A * | 7/1998 | Russo | 128/205.12 |
| 5,791,337 A | 8/1998 | Coles et al. | |
| 5,792,113 A * | 8/1998 | Kramer et al. | 604/167 |
| 5,813,402 A | 9/1998 | Jinotti | |
| 5,855,562 A | 1/1999 | Moore et al. | |
| 5,882,348 A | 3/1999 | Winterton et al. | |
| 5,919,174 A | 7/1999 | Hanson | |
| 6,165,168 A * | 12/2000 | Russo | 604/533 |
| 6,176,234 B1 | 1/2001 | Salter et al. | |
| 6,227,200 B1 * | 5/2001 | Crump et al. | 128/207.16 |

OTHER PUBLICATIONS

U.S. Appl. No. 09/471,317, filed Dec. 23, 1999.
U.S. Appl. No. 09/460,257, filed Dec. 13, 1999.
U.S. Appl. No. 09/459,522, filed Dec. 13, 1999.
U.S. Appl. No. 09/693,261, filed Oct. 20, 2000.
U.S. Appl. No. 09/357,591, filed Jul. 20, 1999.

* cited by examiner

RESPIRATORY SUCTION CATHETER APPARATUS WITH IMPROVED VALVE AND COLLAR

The present application is a continuation application of application Ser. No. 09/157,605 filed Sep. 21, 1998 now abandoned.

BACKGROUND OF THE INVENTION

1. Field of the Invention

The present invention relates to a respiratory suction catheter system with an improved mechanism for cleaning the tip of the catheter without drawing an excessive amount of air from the respiration circuit to which the endotracheal catheter is attached. More specifically, the present invention relates principally to a closed suction endotracheal catheter system which provides improved cleaning of the catheter while minimizing or eliminating air drawn from the patient's respiration circuit.

2. State of the Art

There are a variety of different circumstances under which a person may be required to have an artificial airway, such as an endotracheal tube, placed in his or her respiratory system. In some circumstances, such as surgery, the artificial airway's function is primarily to keep the patient's airway open so that adequate lung ventilation can be maintained during the procedure. In many other situations, however, the endotracheal tube will be left in the patient for a prolonged period of time. For example, with many patients, the endotracheal tube will remain in place to sustain mechanical ventilation for the life of the patient.

If an endotracheal tube is to be left in place for any substantial amount of time, it is critical that respiratory secretions be periodically removed. This is most often accomplished with the use of a respiratory suction catheter. As the suction catheter is withdrawn, a negative pressure is applied to the interior of the catheter to draw mucus and other secretions from the respiratory system. While a substantial amount of the mucus and other secretions will be withdrawn through the catheter lumen, a portion of the mucus and other secretions remain on the outside of the catheter.

Because patient secretions can contain infectious diseases, such as streptococcus, pseudomonus, staphylococcus and even HIV, it is important to shield clinicians from them. Likewise, it is important to shield patients from communicable pathogens in the environment. This is particulary important because such patients often have compromised immune systems.

In addition to concerns of cross-contamination, suctioning patients' artificial airways potentially interferes with proper respiration. The most common group of patients who have indwelling endotracheal tubes for prolonged periods are those who must be mechanically ventilated. Mechanically ventilated patients will typically have a fitting or manifold attached to the proximal end of the endotracheal tube (i.e. the end extending outside the patient) at an endotracheal tube hub. A pair of ventilator tubes extend from a mechanical ventilator and are typically attached to the manifold by an adapter. One tube provides inspiratory air to the patient for inhalation. The other tube allows for exhaled or expiratory air to exit the system.

Until the 1980s, it was common to disconnect the patient from the manifold and ventilator tubes each time the patient needed to be suctioned. Interference with the air supply to the patient, even if only for a few seconds, was often unnecessarily distressing to the patient. These problems were initially overcome in the invention disclosed in U.S. Pat. No. 3,991,762 to Radford. Radford developed what is commonly referred to as a closed suction catheter system. In a closed suction catheter system, a catheter is maintained within a protective sleeve which is attached to the manifold. When suctioning is desired, the catheter is advanced through the manifold and into the artificial airway. Negative pressure is then applied to the catheter and secretions within the patients respiratory system are evacuated. Improvements were made to the system by the invention disclosed in U.S. Pat. No. 4,569,344 to Palmer. Palmer improved the system by reducing the risk of cross-contamination between the patient and the medical personnel using the device. Since that time, there has been a significant shift toward the use of closed suction catheter systems.

The advantage of closed suction catheters is that the ventilating circuit is not detached from the patient during suction procedures, as it is during open suction procedures. Because the catheter is reused a number of times over a twenty-four hour period, it is important that mucus and other secretions be cleaned from the catheter prior to periods of non-use. If the secretions are not removed, the risk of auto-contamination increases. It is also important to clean the lumen of the catheter to maintain suction efficiency.

There are several mechanisms by which the catheter may be cleaned. First, in U.S. Pat. No. 4,569,344, there is shown a lavage port which enables the user to inject liquid into the area surrounding the distal end of the catheter after it has been withdrawn from the patient. When liquid is injected into the closed suction catheter apparatus and suction is applied, the liquid helps to loosen and remove the secretions from the exterior of the catheter.

One significant problem with simply injecting liquid and applying suction to remove it, is that the suction also causes a volume of respiratory air to be removed through the catheter. In a "closed system", the air that is evacuated potentially disrupts the carefully controlled ventilatory cycles. Thus, the amount of respiratory air available to the patient is potentially decreased as a result of catheter cleaning. If the clinician has a hard time cleaning secretions from the catheter, suction may be applied through the catheter several times—thereby repeatedly drawing air from the ventilatory circuit.

Other closed suction catheters have been developed to have a cleaning or lavage chamber which is physically isolated from the respiration circuit. For example, in U.S. Pat. No. 5,487,381 to Jinotti, there is shown a closed suction catheter which has a lavage chamber configured to receive the distal tip of the catheter as it is withdrawn from the manifold. A wall is then slid from an open position to a closed position to isolate the distal end of the catheter from the manifold and the respiration circuit. A port is commonly provided to inject lavage solution into the cleaning chamber.

One problem which is present in such a configuration is that there is a lack of air to allow the suction catheter to clean properly. The application of negative pressure in the catheter can create a vacuum within the chamber in the absence of sufficient air flow into the chamber. Thus, isolating the chamber inhibits free evacuation of the cleaning solution. Further, in one presently available product, the cleaning liquid commonly remains in the catheter due to the lack of airflow. Thus, contaminated liquids remaining in the catheter lumen can be reintroduced to the patient when the cleaning chamber is opened.

In addition to the above concerns, the closed suction catheters presently available suffer from the inability to clean the catheter tip to the most desirable extent. If pathogens or other contaminants remain on the catheter for too long, they can auto-contaminate the patient. Additionally, if mucus and other secretions dry on the catheter, they can interfere with the suction efficiency, present an unsightly appearance and necessitate premature replacement of the closed suction catheter apparatus. Thus, there is a need for a catheter apparatus which has a mechanism for more effectively cleaning the distal end of the catheter without creating a substantial draw on respiratory air in the ventilation circuit.

SUMMARY OF THE INVENTION

Thus, it is an object of the present invention to provide an improved respiratory suction catheter apparatus which minimizes the amount of air drawn from the ventilation circuit during cleaning of the distal end of the catheter.

It is another object of the present invention to provide such a respiratory suction catheter apparatus which improves removal of mucus and other secretions from the distal tip of the catheter.

It is yet another object of the present invention to provide such a respiratory suction catheter apparatus wherein the mechanisms for improving cleaning function automatically to separate a cleaning chamber from the ventilation circuit.

It is still another object of the present invention to provide such a respiratory suction catheter apparatus which causes cleaning to be effected in a turbulent fluid flow.

It is a further object of the present invention to provide such a respiratory suction catheter apparatus which is easy to use and relatively inexpensive.

The above and other objects of the invention are realized in specific illustrated embodiments of an improved respiratory suction catheter apparatus which includes a manifold for attachment to an artificial airway, such as an endotracheal tube, to form a ventilation circuit, a catheter which is displaceable through the manifold and into the artificial airway to suction secretions from the artificial airway and lungs, and a valve mechanism disposed adjacent the ventilation circuit to minimize the air drawn from the respiration circuit of a patient while the catheter is being cleaned.

In accordance with one aspect of the invention, the valve mechanism is configured to automatically engage the catheter tip after it is withdrawn through the manifold to thereby minimize the amount of air drawn into the catheter during cleaning.

In accordance with another aspect of the present invention, the valve mechanism is provided with an air makeup to allow makeup air into the catheter and thereby ensure proper evacuation of secretions, and any liquid used to clean the catheter.

In accordance with another aspect of the present invention, an air turbulence enhancing mechanism is provided for increasing turbulent airflow around the distal end of the catheter to thereby improve removal of secretions from the catheter.

In accordance with still another aspect of the present invention, an air makeup mechanism is disposed so as to provide makeup air to the distal end of the catheter which is not drawn from the ventilation circuit.

BRIEF DESCRIPTION OF THE DRAWINGS

The above and other objects, features and advantages of the invention will become apparent from a consideration of the following detailed description presented in connection with the accompanying drawings in which:

FIG. 4C shows a fragmented, cross-sectional view of the embodiment of FIGS. 4A and 4B, with an air makeup mechanism in an open position to facilitate suctioning of mucus and the like;

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 1:
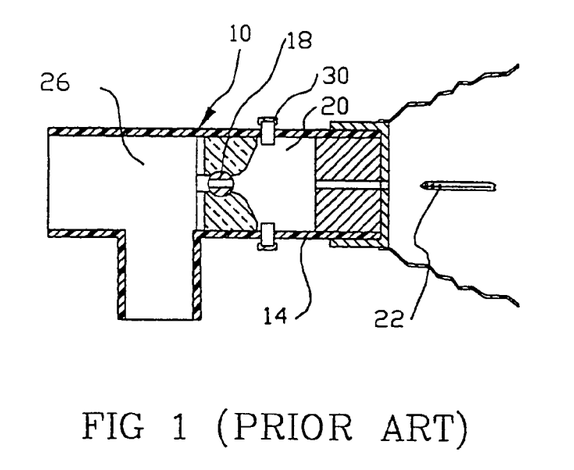
FIG. 1 shows a cross-sectional view of a manifold and catheter cleansing mechanism in accordance with the teachings of the prior art.

Referring to FIG. 1, there is shown a cross-sectional view of a manifold 10 and catheter cleansing mechanism 14 in accordance with the teachings of the prior art. The manifold 10 has a valve mechanism in the form of a rotatable rod 18 for selectively isolating a lavage chamber 20 from the ventilation circuit 26. When the distal end of the catheter 22 is disposed in the lavage chamber 20, a lavage solution can be injected through a side port 30 to help wash the mucus and other secretions from the exterior of the catheter 22. Because of the relative size and dimensions of the lavage chamber 20, however, there is nothing to force vigorous interaction between the lavage solution and the secretions on the exterior of the catheter. Additionally, because the lavage chamber is not configured for makeup air to enter when the rotatable rod 18 is closed, a vacuum can be created in the lavage chamber 20 which interferes with effective suctioning.

An additional disadvantage of the embodiment shown in FIG. 1 is that the closure mechanism for such devices must typically be manually activated. If the user fails to close the rotatable rod 18, actuation of suction through the catheter will draw air from the ventilation circuit 26.

Figure 2:
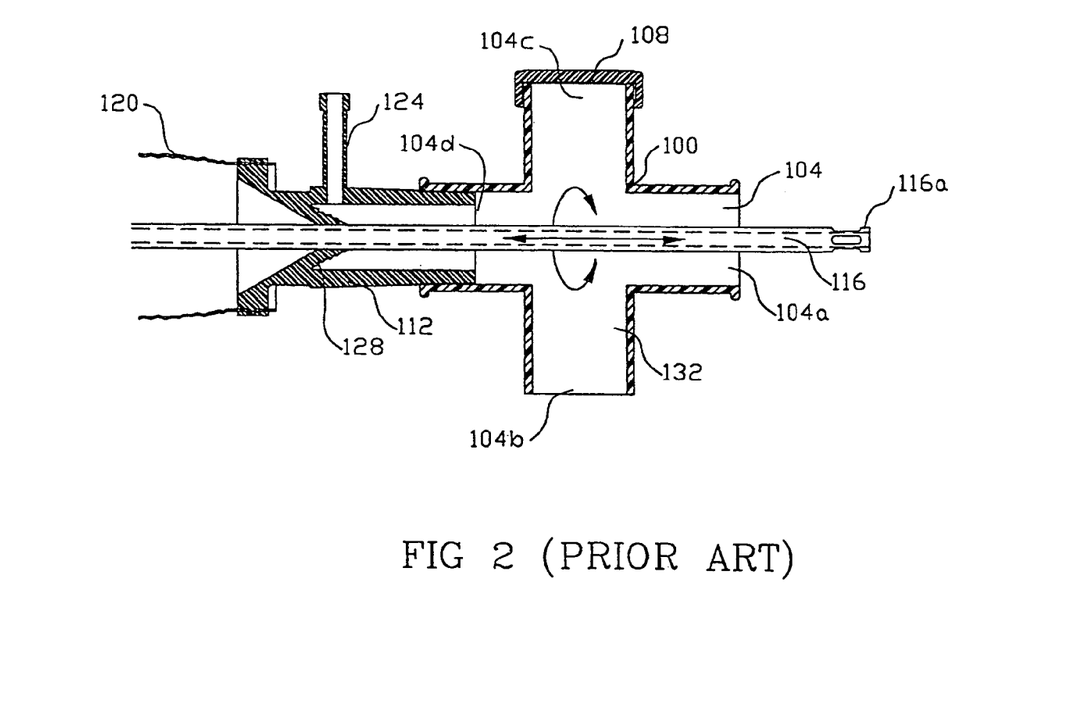
FIG. 2 shows a cross-sectional view of a manifold and catheter cleaning mechanism in accordance with the teachings of another embodiment of the prior art.

Turning now to FIG. 2, there is shown a cross-sectional view of an alternative embodiment of the prior art. The manifold 100 is provided with a plurality of ports 104. A first port 104a is attached to the hub of an endotracheal tube of the patient to conduct respiratory air to and from the endotracheal tube. Thus, the manifold forms part of a respiration circuit. The air is typically provided to and removed from the manifold through a second port 104b which is attached to a pair of ventilation tubes via a connector (not shown). The ventilation tubes are, in turn, connected to a mechanical ventilator (not shown) in a manner which will be well known to those skilled in the art.

A third port 104c is provided opposite the second port 104b. The third port 104c is typically covered with a cap 108 which is removed when "blow-by" is desired to wean a patient from forced ventilation.

The manifold also has a fourth port 104d. A coupling 112 is configured to form a force-fit engagement with the fourth port 104d and effectively connects the catheter 116 and a protective sleeve 120 to the manifold 100. Disposed at a proximal end of the coupling 112 is a lavage port 124 through which a cleaning liquid can be injected to rinse the exterior of the catheter 116. Such a configuration is advantageous because the lavage port 124 is positioned adjacent a seal 128 which is configured to wipe mucus and other secretions from the catheter 116 as is drawn through the seal. Thus, a user will typically withdraw the catheter 116 until the distal end 116a thereof is positioned slightly distally of the seal 128, and then the cleaning solution will be injected into the lavage port 124 to assist in the removal of secretions. While such a method of removing the secretions is generally effective, it draws air from the ventilation circuit 132. Additionally, it is common for respiratory therapists and other clinicians to maintain the suction on as the distal end 116a of the catheter 116 is drawn from the first port 104a to a position immediately adjacent the seal 128.

Figure 3A:
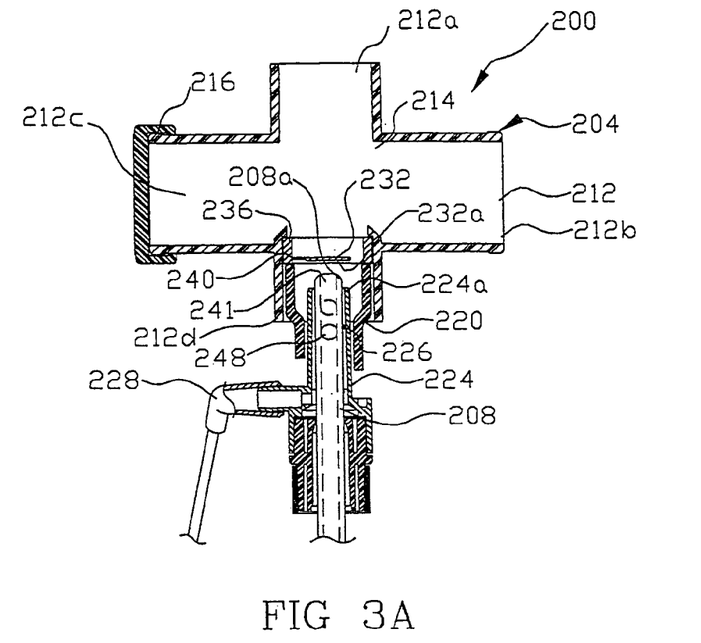
FIG. 3A shows a cross-sectional view of the manifold and catheter of an improved respiratory suction catheter apparatus with a valve member in an open position in accordance with the principles of the present invention.

Turning now to FIG. 3A, there is shown a cross-sectional view of a portion of an improved endotracheal catheter, generally indicated at 200. The endotracheal catheter includes a manifold, generally indicated at 204, and a catheter 208. The manifold 204 includes a plurality of ports 212a–c. A first port 212a is configured for attachment to the proximal end of an artificial airway, such as the hub of an endotracheal tube, tracheostomy tube, etc. A second port 212b is typically connected to a pair of ventilator tubes (not shown) by means of an adaptor (not shown), in accordance with common practice in the art. During normal usage, conditional inspiratory air is forced through one of the ventilator tubes, through the second port 212b and the first port 212a and into the patient's lungs via the artificial airway. Exhaled air is carried through the first port 212a and then the second port 212b and out through the other ventilator tube. Thus, the manifold 204 forms part of a respiration circuit 214 through which respiratory air is cycled.

Also forming part of the manifold 204 is a third port 212c. The third port 212c is typically covered by a cap 216. Whenever mechanical ventilation is used, it is the goal to someday return the patient to voluntary or spontaneous breathing. To accomplish this, the patient must usually be weaned from the mechanical ventilation—to spontaneous breathing. To this end, the cap 216 may be removed from the third port 212c so that oxygenated air is passed by the patient's endotracheal tube, but inspiratory air is not forced into the patient by means of a totally closed circuit. This situation, commonly called "blow-by," enables the patient to gradually resume natural or spontaneous breathing.

The manifold 204 also has a fourth port 212d. The fourth port 212d is disposed generally opposite the first port 212a and is configured to allow the catheter 208 to slide therethrough and into the first port to enable suctioning of the patient. At the completion of suctioning, the catheter 208 is pulled back into the fourth port 212d to prevent interference with the respiration circuit 214.

Disposed between the wall forming the fourth port 212d and the catheter 208 is a coupling or adapter 220. On an outer extreme, the adapter 220 engages the wall defining the fourth port 212d. On an inner extreme, the adapter 220 engages a collar 224 which closely surrounds the catheter 208 so as to leave a small cylindrical space 226 around the catheter 208. Ideally the space between the catheter 208 and the collar 224 is between 0.005 and 0.015 inch. This proximity provides two important advantages. First, if lavage needs to be provided to the lungs of the patient, injecting lavage solution through the lavage port 228 and into the cylindrical space 226 causes a stream of lavage solution to be directed out the distal end 224a of the collar, and through the first port 212a. If the spacing between the catheter 208 and the collar 224 is too large (as in the art discussed above), the lavage solution cannot not be thus directed. Second, as the catheter 208 is drawn back into the collar 224 after use, the collar helps to wipe any heavy layers of mucus or other secretions from the outside of the catheter. Injecting lavage/cleaning solution through the lavage port 228 further removes the secretions from the exterior of the catheter 208 and enhances evacuation by suction in the catheter. This configuration also minimizes the volumes of air and cleaning solution necessary to effect cleaning.

While the collar 224 configuration shown in FIG. 3A is beneficial, it is still common to have secretions build up on the distal end 208a of the catheter 208. If such build up is not promptly removed, it can interfere with the ability of the catheter to properly suction the patient. It can also serve as a culture medium for pathogens within the closed suction catheter system.

In accordance with one of the principles of the present invention, it has been found that selective obstruction of the airflow into the distal end 208a of the catheter 208 significantly improves catheter cleaning. Additionally, it has been found that such a mechanism for improved cleaning also minimizes the withdrawal of air from the respiration circuit 214.

As shown in FIG. 3A, a flap 232 is hingedly attached to an annular ring 236 disposed inside the fourth port 212d so as to enable the flap 232 to pivot with respect to the ring. Of course, the flap 232 could be attached directly to the wall of the manifold 204 defining the fourth port 212d or to the adapter 220. The hinged attachment 240 allows the flap 232 to selectively move while maintaining alignment with the catheter tip, thereby creating a flap valve.

Figure 3B:
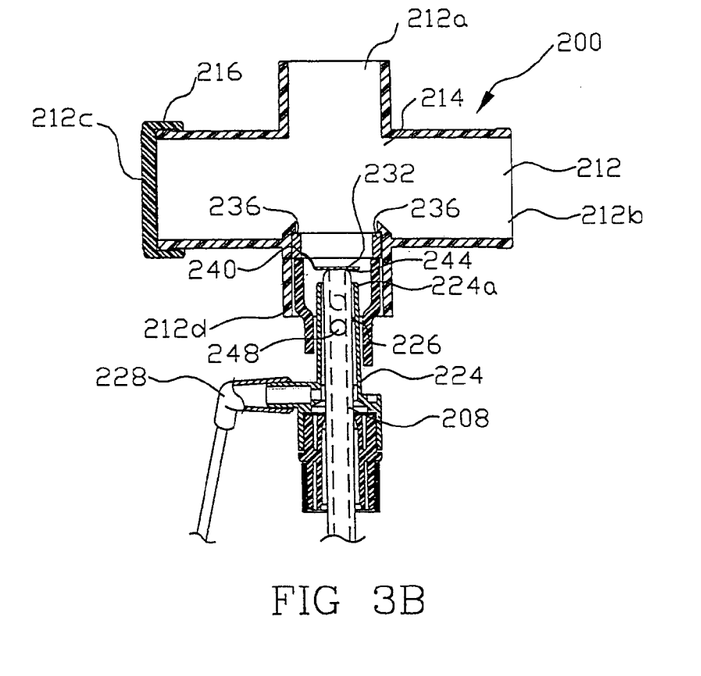
FIG. 3B shows a cross-sectional view of the manifold and catheter shown in FIG. 3A, with the valve in a second, closed position.

As shown in FIG. 3B, the flap 232 is positioned to align with the distal end 208a of the catheter 208 when the catheter is almost completely withdrawn into the collar 224. The hinged attachment 240 is sufficiently flexible that suction through the distal end 208a of the catheter 208 will draw the flap 232 into contact with the distal end of the catheter. As with most closed suction catheters, the catheter 208 includes a primary aperture 244 in the distal end 208a and one or more lateral apertures 248 positioned slightly proximal from the distal end.

When the flap 232 moves proximally and contacts the distal end 208a of the catheter 208, suction through catheter tip aperture 244 is dramatically reduced or eliminated. Decrease in suction flow through the aperture 244 causes increased suction flow in the lateral apertures 248, thereby increasing the ability of the lateral apertures to evacuate any secretions contained between the outside of the catheter 208 and the interior of the collar 224. Because the lateral apertures 248 are generally smaller than the distal aperture 244 and because airflow to the lateral apertures is limited by the collar 224, a substantial decrease in the amount of air drawn from the respiration circuit is achieved while simultaneously improving cleaning of the catheter 208.

As shown in FIGS. 3A and 3B, the proximal side 232a (i.e. the side opposite the respiration circuit 214) of the flap 232 is generally planar. In such a configuration, the proximal side 232a of the flap 232 will typically form a substantially complete seal with the distal end 208a of the catheter 208.

Figure 3C:
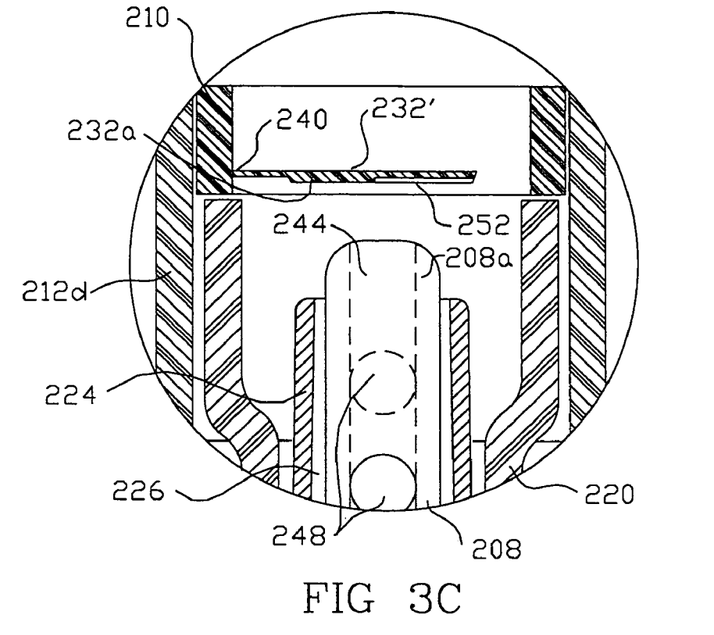
FIG. 3C shows a fragmented, close-up cross-sectional view of one embodiment of the improved respiratory suction catheter apparatus shown in FIG. 3A.

Turning now to FIG. 3C, there is shown a close-up cross-sectional view of the embodiment shown in FIGS. 3A and 3B with a slight modification to the flap 232. Unlike the flap 232 in FIGS. 3A and 3B which is substantially planar, the flap 232' in FIG. 3C has a channel 252 formed therein on the proximal side 232a'. The channel 252 prevents the flap 232' from forming an airtight engagement with the distal end 208a of the catheter 208. In other words, the channel 252 ensures that a measured volume of air will be drawn into the aperture 244 at the distal most end of the catheter.

The volume of air drawn through the channel 252 can have an important affect. Specifically, the air creates turbulent airflow both within the catheter 208 and immediately around its exterior. The turbulent airflow, in turn, assists in breaking up agglomerations of mucus and secretions which lavage/cleaning solution alone may not. Thus, the turbulent airflow helps to provide improved cleaning of the distal end 208a of the catheter 208.

This is in sharp contrast to many of the prior art devices which have advocated the use of a lavage/cleaning chamber to clean the exterior of the catheter. Because the lavage/cleaning chamber is usually substantially larger than the catheter or because makeup air is not specifically provided, it is difficult to create turbulent airflow within the chamber. Without turbulent airflow, the mucus and other secretions are often not removed from the exterior of the catheter.

Figure 3D:
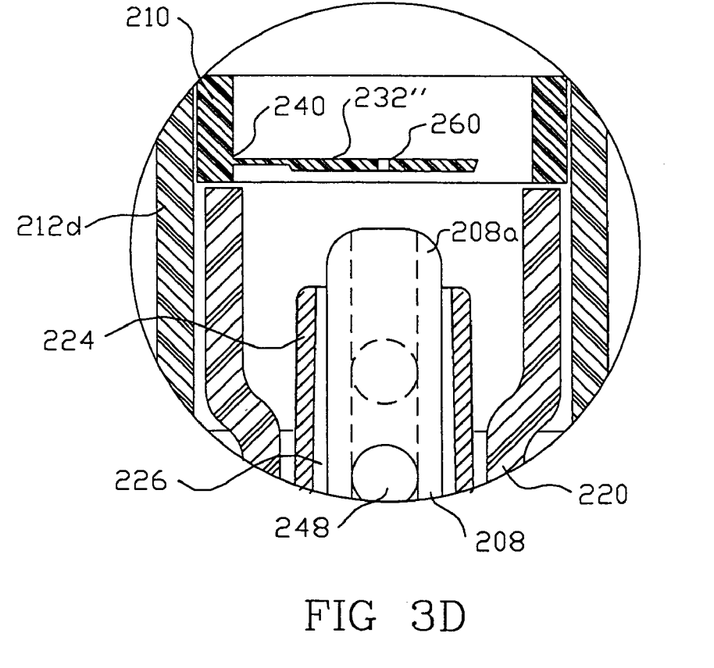
FIG. 3D shows a fragmented, close-up cross-sectional view of another embodiment of the improved respiratory suction catheter apparatus shown in FIG. 3A.

Turning now to FIG. 3D, there is shown yet another variation of the flap 232 shown in FIGS. 3A and 3B. Rather than having a channel formed in a proximal side thereof, the flap 232" has an aperture 260 formed therein so as to allow a relatively small amount of air to pass through the flap 232". As with the embodiment of FIG. 3C, the small hole creates turbulent airflow at the distal end 208a of the catheter 208 and thereby improves cleaning. It is currently believed that an aperture 260 in the flap 232" with a diameter of about 0.02 is preferred.

Figure 3E:
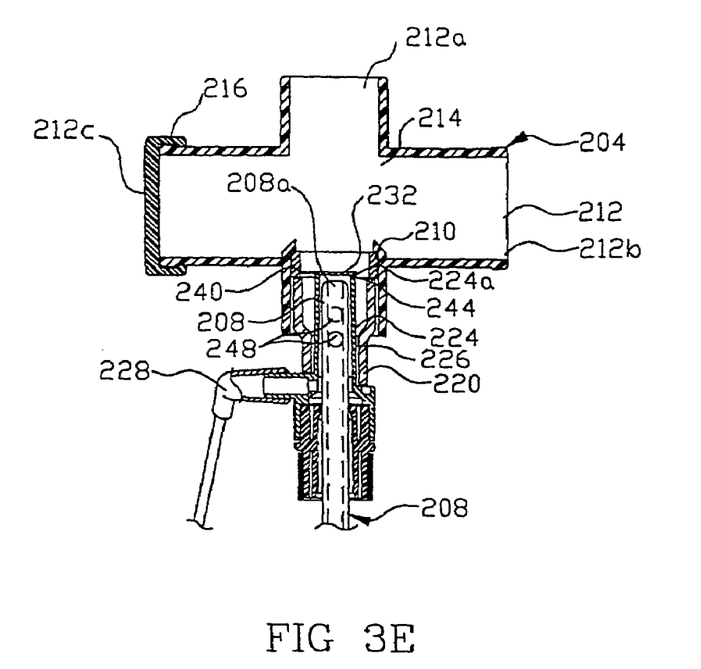
FIG. 3E shows a cross-sectional view of an embodiment similar to those shown in FIGS. 3A through 3D, but wherein the flap engages the collar.

While shown in FIGS. 3A through 3D as engaging the distal end 208a of the catheter 208, the flap 232 forming a flap valve need not engage the catheter itself. Thus, for example, FIG. 3E shows an embodiment similar to those shown in FIGS. 3A through 3D, except that the flap 232 is disposed to engage the distal end 224a of the collar 224 rather than the distal end 208a of the catheter 208. In such a configuration, suction flow can still be achieved through the aperture 244 at the distal end 208a of the catheter 208.

Preferably, a source of makeup air will be provided. This can be accomplished by using either of the flap configurations shown in FIGS. 3C and 3D. In the alternative, a small hole can be formed in the collar 224 to facilitate a small amount of makeup air being present to enhance suction flow and to increase turbulence.

Regardless of which configuration of those shown in FIGS. 3A through 3E is used, the result is an improved ability to clean the distal end 208a of the catheter 208, while at the same time significantly reducing the amount of air which is withdrawn from the respiration circuit 214. Thus, consistent ventilation is provided to the patient, and the clinician is able to more easily clean the catheter 208.

Figure 4A:
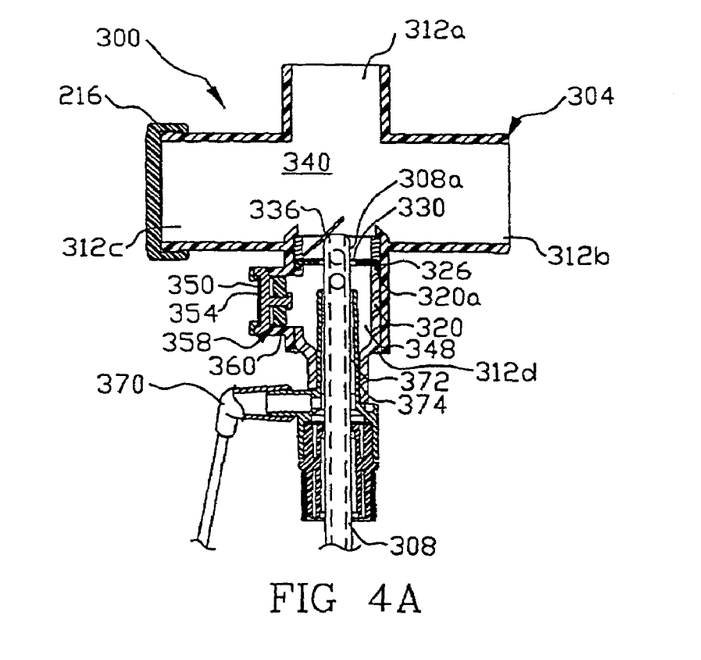
FIG. 4A shows a fragmented, cross-sectional view of an alternative embodiment of an improved respiratory suction catheter apparatus having a valve in an open position in accordance with the principles of the present invention.

Turning now to FIG. 4A, there is shown another embodiment of an improved respiratory suction catheter apparatus, generally indicated at 300, made in accordance with the principles of the present invention. The improved respiratory suction catheter apparatus 300 includes a manifold 304 and a catheter 308. As with the previous embodiment, the manifold 304 includes a first port 312a, a second port 312b, a third port 312c and a fourth port 312d.

An adapter 320 is disposed in the fourth port 312d in such a manner as to make the manifold 304 and the catheter 308 a functionally integrated unit. The adapter 320 may be adhesively attached to the manifold 304, or may be simply force-fit.

Unlike the embodiment discussed with FIGS. 3A through 3D, an annular ring is not disposed in the manifold 304 independent of the adapter 320. Rather, an annular ring 326 extends inwardly from a distal end 320a of the adapter 320'. The annular ring 326 defines an aperture or opening 330 through which the catheter 308 can be extended. Thus, the opening 330 is slightly larger than the exterior of the catheter 308.

Also extending inwardly from the adapter 320 is a flap 336. The flap 336 is preferably hingedly attached to either the adapter directly or to the annular ring 326. When no suction is applied to the catheter 308, or when the distal end 308a of the catheter is disposed distally from the flap 336, the flap will generally extend distally from the annular ring 326 and provide virtually no resistance to advancement of the catheter 308.

Figure 4B:
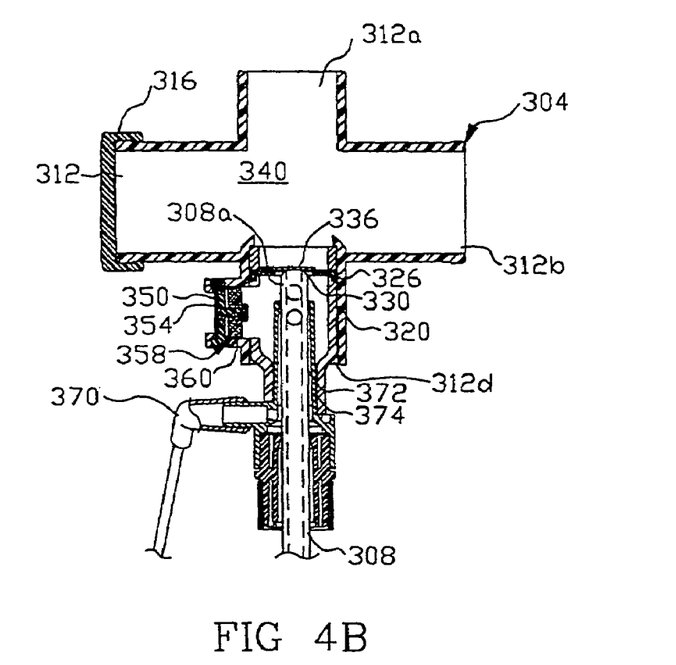
FIG. 4B shows a fragmented, cross-sectional view of the embodiment of FIG. 4A, wherein the valve is in a closed position to isolate the catheter from the ventilation circuit.

As shown in FIG. 4B, as the distal end 308a of the catheter 308 is withdrawn through the annular ring 326 while suction is applied, a vacuum is created which pulls the flap 336 over the opening 330, thereby isolating the distal end 308a of the catheter 308 from the ventilation circuit 340 and preventing the catheter from drawing air away from a patient to whom the manifold is attached. While the flap 336 could be configured in the manner shown in FIGS. 3C and 3D, the present configuration does not necessitate the use of makeup air from the ventilation circuit 340.

If the catheter 308 were simply left in the chamber 348 behind the flap 336/annular ring 326 and lavage were injected into the chamber, a substantial negative pressure could build within the chamber. Additionally, because no relief is provided, it would be difficult to suction any mucus etc. from the chamber once the lavage source had been sucked dry.

Figure 4C:
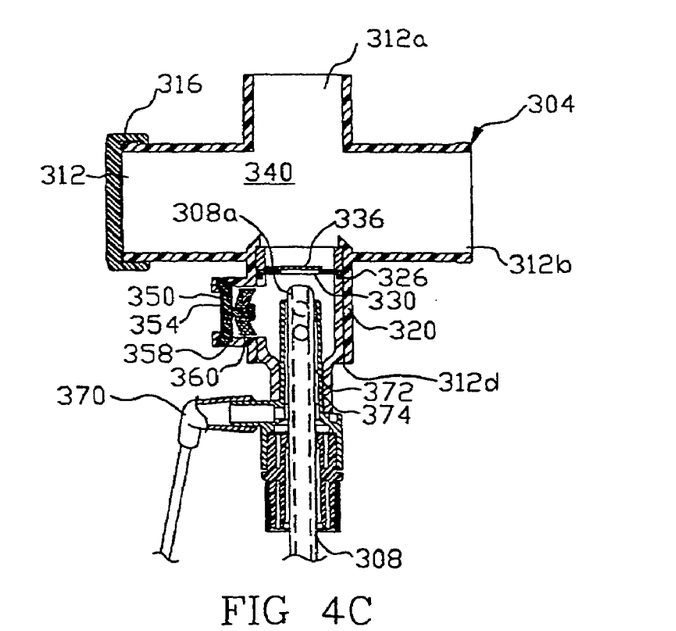

To overcome these problems with the prior art, the embodiment in FIGS. 4A through 4C has a makeup air inlet, generally indicated at 350 which is formed in a portion of the wall defining the fourth port 312d of the manifold and the adapter 320. The makeup air inlet 350 preferably includes a filter 354 which is selected to substantially prevent cross-contamination between the environment/clinicians and the patient. Disposed adjacent to the filter material is a flexible barrier 358 which forms a one-way valve 360.

As shown in FIG. 4C, the one-way valve 360 will generally be closed when the catheter 308 is in an extended position, wherein the catheter extends through the opening 330 in the annular ring 326. However, once the distal end 308a of the catheter 308 has been withdrawn through the opening 330 in the annular ring 326 and the flap 336 has been drawn closed, a vacuum will quickly develop on the side of the flap 336 opposite the respiration circuit 340. The vacuum causes the one-way valve 360 to open and allow a supply of makeup air to enter the chamber. The makeup air flowing past the flexible one-way valve member 360, helps to create turbulent airflow and facilitate removal of any respiratory secretions on the catheter 308. This is preferably accomplished at about the same time the user utilizes the lavage port 370 to inject lavage/cleaning solution through the space 372 between the collar 374 and the catheter 308. It will be appreciated that the one-way valve 360 could be configured to provide very little resistance to air inflow, or could be configured to require a substantial vacuum to be present before makeup air is allowed into the area proximal the flap 336.

Figure 5A:
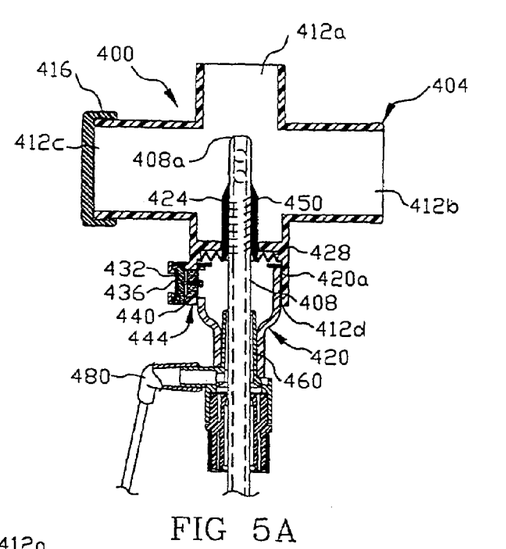
FIG. 5A shows a cross-sectional view of an alternative embodiment of an improved respiratory suction catheter apparatus having a valve in an open position in accordance with the principles of the present invention.

Turning now to FIG. 5A, there is shown a fragmented, cross-sectional view of an alternative embodiment of an improved respiratory suction catheter apparatus, generally indicated at 400. The respiratory suction catheter apparatus includes a manifold 404 and a catheter 408 which is moveable through the manifold to suction secretions from a patient's lungs. As with the previously discussed embodiments, the manifold includes a first port 412a for attachment to an endotracheal tube or other artificial airway, a second port 412b for attachment to the ventilator tubes of a mechanical ventilator, a third port 412c which is covered with a cap 416, and a fourth port 412d which receives the connector or adaptor 420.

Disposed at the distal end 420a of the adaptor 420 is a valve 424 in a configuration which is commonly referred to as a duckbill valve. The valve 424 is formed by a piece of resilient material which opens as the catheter 408 is advanced therethrough, and closes when the catheter is withdrawn. The valve 424 is attached to the adaptor 420 by a flexible base 428.

Figure 5B:
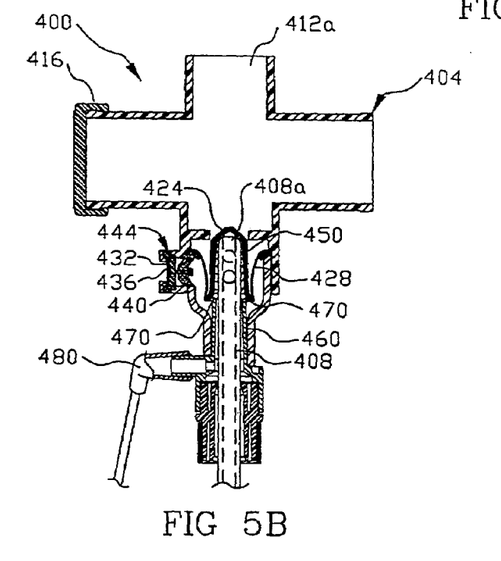
FIG. 5B shows a cross-sectional view of the embodiment shown in FIG. 5A with the valve in a closed position.
Figure 5C:
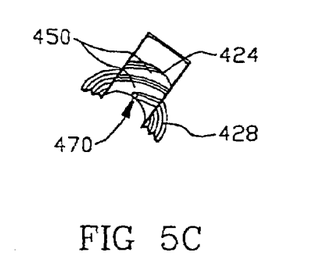
FIG. 5C shows a partial cross-sectional view of the valve of the embodiment shown in FIGS. 5A and 5B.

Also disposed in the adaptor 420 is an air inlet 432 which includes a filter material 436 and a resilient member 440 configured to form a one-way valve 444 similar to that discussed in the previous embodiment. While duckbill valves have been used in endotracheal catheter systems in the past, the valve 424 shown in FIGS. 5A through 5C is substantially advanced in several respects. First, as shown in FIGS. 5A and 5C, the interior of the valve 424 has helical grooves 450 formed therein. The helical grooves 450 help to create turbulent airflow around the distal end 408a of the catheter 408. Additionally, the flexible base 428 is configured to allow the valve 420 to be drawn toward the collar 460 to thereby reduce space and improve removal of secretions from the exterior of the catheter 408.

Turning now specifically to FIG. 5B, there is shown a cross-sectional view similar to that shown in FIG. 5A, but with the distal end 408a of the catheter 408 in a retracted position. Once the distal end 408a of the catheter 408 is withdrawn proximally from the valve 424, the suction through the catheter works against the flexible base 428 of the valve and draws the valve toward the collar 460. A pair of air inlets 470 are disposed at the base 428 of the valve 424 and allow air into the valve.

Applying suction to the valve 424 and through the air inlets 470 as shown in FIG. 5B creates a vacuum between the adaptor 420 and the flexible base 428, thereby causing the one-way valve 444 to open and allow air into the air inlets 470 at the top of the collar 460. This air mixes with the water injected through the lavage port 480 and turbulently travels along the distal end 408a of the catheter 408. The turbulent motion of the air/water mixture is enhanced by the helical grooves 450.

Once suction through the catheter 408 is stopped, there is no longer a negative pressure to keep the flapper valve 444 open, or to maintain the valve 444 adjacent to the distal end of the collar. Thus, the valve 424 will return to the position shown in FIG. 5A, except that it will be closed as the catheter 408 remains substantially in the collar until the next use.

Figure 6A:
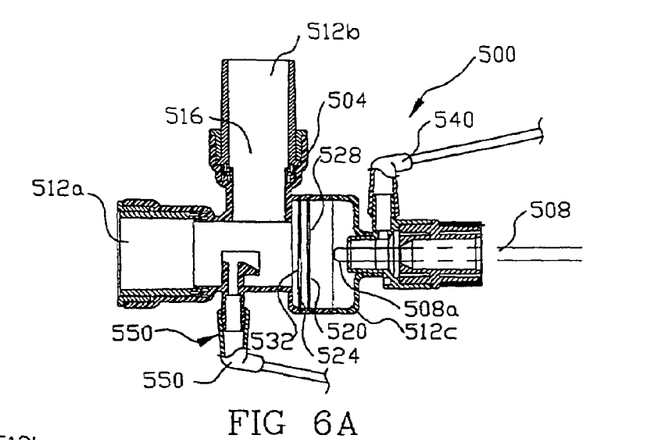
FIG. 6A shows a cross-sectional view of yet another alternative embodiment of an improved respiratory suction catheter apparatus made in accordance with the principles of the present invention.

Turning now to FIG. 6A, there is shown a cross-sectional view of yet another alternative embodiment of an improved endotracheal catheter made in accordance with the principles of the present invention. The endotracheal catheter 500 includes a manifold 504 and a catheter 508. The manifold 504 has a first port 512a for attachment to the hub of an artificial airway of a patient, and a second port 512b for attachment to the ventilator tubes (not shown) of a mechanical ventilator so as to define a ventilation circuit 516.

Figure 6B:
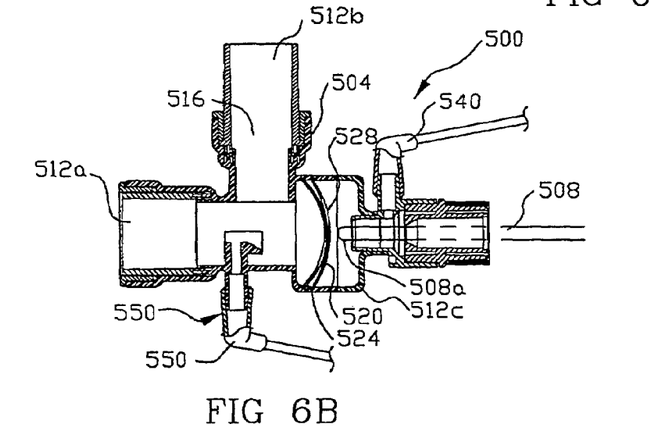
FIG. 6B shows a cross-sectional view of the embodiment shown in FIG. 6A in a closed configuration.
Figure 6C:
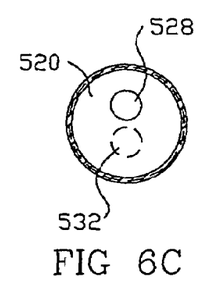
FIGS. 6C and 6D show end views of the valve mechanism of the embodiment shown in FIGS. 6A and 6B in a relaxed position and with a catheter extending therethrough, respectively.
Figure 6D:
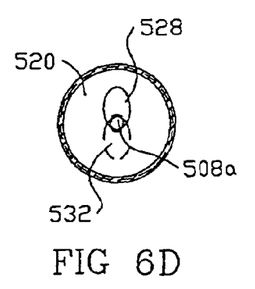

The manifold also includes a third port 512c which is configured to receive the catheter 508. Disposed in the third port 512c are a pair of floating flexible disks or membranes 520 and 524. Each of the disks defines an aperture or opening 528 and 532, respectively, through which the catheter 508 may be slid. An end view of the disks 520 and 524 with the catheter being slid therethrough is shown in FIG. 6D.

When the catheter 508 is withdrawn through the openings 528 and 532 in the disks, a vacuum is created proximally of the disks 520 and 524. The vacuum draws both of the disks toward the end of the catheter 508, as shown in FIG. 6B. This substantially seals the two disks together in an arrangement without overlapping openings as shown in FIGS. 6B and 6C. This configuration minimizes or eliminates (depending on the seal) air flow out of the respiration circuit as lavage solution is injected through the lavage port 540 and the distal end 508a of the catheter 508 is cleaned.

Because the lavage port 540 is disposed behind the disks 520 and 524 which provide a significant impediment to lavage flowing to the lungs if needed, a second lavage port 550 can be added distally from the disks. The second lavage port 550 would typically not be used for cleaning of the catheter 508.

Figure 7A:
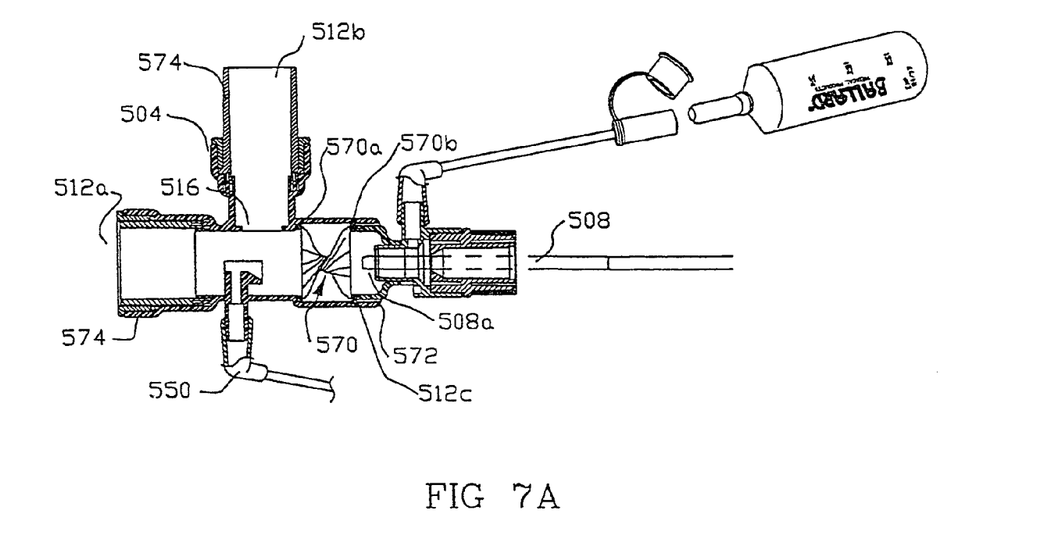
FIG. 7A shows a cross-sectional view of still another embodiment of an improved respiratory suction catheter apparatus made in accordance with the principles of the present invention.

Turning now to FIG. 7A there is shown a cross-sectional view of still another embodiment of an improved endotracheal catheter made in accordance with the principles of the present invention. Most portions of the endotracheal catheter shown in FIG. 7A are the same as those discussed with respect to FIGS. 6A through 6D and are numbered accordingly. The one major difference between the embodiments of FIGS. 6A through 6D and FIG. 7A is that the disks 520 and 524 of the previous embodiment are replaced with a resilient closing membrane 570 which is attached at one end 570a to the manifold 504 and at an opposing end 570b to an adapter 572 holding the catheter 508. The adapter 572 or manifold 504 can be rotated to twist the membrane 570 and thereby either reduce or enlarge the size of a hole 580 (FIG. 7B) formed by the material. By twisting the resilient material 570 to close the hole 580, the drawing of air from the respiration circuit 516 can be reduced or even eliminated.

When suctioning of patient is desired, the resilient material 570 is rotated to allow the catheter to pass therethrough. Because swivels 574 are disposed on the first and second ports 512a and 512b, the rotation of the resilient material to expand or contract the hole therethrough will provide virtually no discomfort to the patient, while effectively controlling the amount of air which is drawn from the respiration circuit 516 when the distal end 508a of the catheter 508 is being cleaned.

Figure 7B:
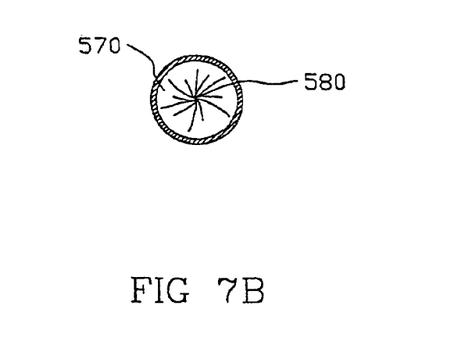
FIG. 7B shows a partial end view of the improved respiratory suction catheter apparatus of FIG. 7A in a closed position.

FIG. 7B shows an end view of the resilient membrane 570. By rotating the resilient membrane 570 in one direction, the hole 580 is enlarged. By rotating the resilient material in an opposing direction, the size of the hole 580 is reduced.

Figure 8A:
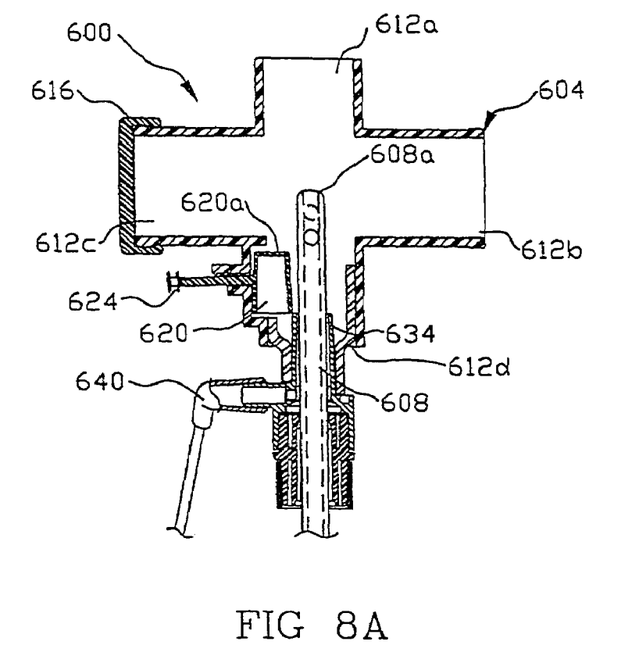
FIG. 8A shows a cross-sectional view of still yet another embodiment of an improved respiratory suction catheter apparatus made in accordance with the principles of the present invention.
Figure 8B:
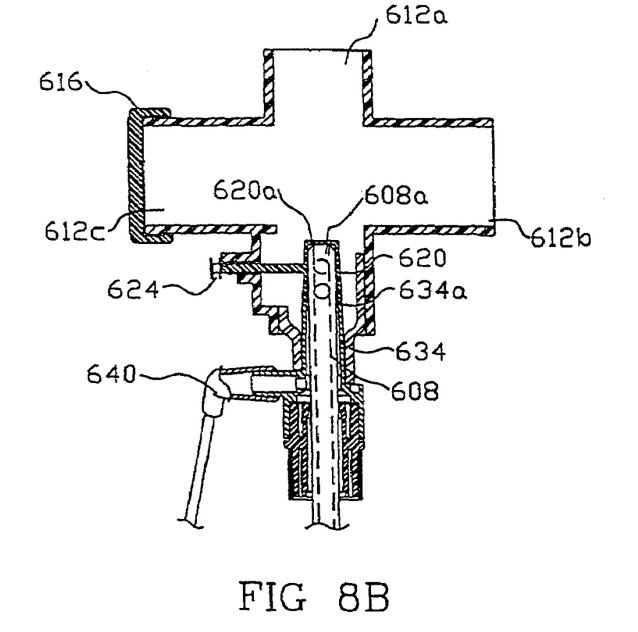
FIG. 8B shows a cross-section view of the improved endotracheal catheter of FIG. 8A, wherein the valve mechanism is in a closed configuration.

Turning now to FIGS. 8A and 8B, there is shown yet another endotracheal catheter embodying principles of the present invention. The respiratory suction catheter apparatus 600 includes a manifold 604 and a catheter 608 which is moveable through the manifold. As with many of the embodiments discussed previously, the manifold 604 includes a first port 612a for connection to the hub of an endotracheal tube, a second port 612b for connection (via ventilator tubes) to a mechanical ventilator, and a third port 612c and cap 616 which can be used for blow-by.

The fourth port 612d is different from those discussed previously because it has a shroud 620 placed therein. The shroud 620 is attached to a plunger 624 so as to allow the user to move the shroud between a first position adjacent the sidewall of the fourth port 612d (FIG. 8A) and a second position (FIG. 8B) wherein the shroud is disposed approximately at the center of port 612d.

During use of the respiratory suction catheter apparatus 600, the shroud 620 will typically be moved into the first position so that it does not interfere with advancement of the catheter 608 through the manifold 604. Once suctioning has been completed, the catheter 608 is withdrawn into the collar 634. The plunger 624 is then pressed so as to move the shroud 620 over the distal end 634a of the collar 634 to cover the distal end 608a of the catheter 608. Typically, the catheter 608 will then be advanced toward the distal end 620a of the shroud 620. Lavage/cleaning solution will then be applied through the lavage port 640 while suction is applied.

If desired, a small gap can be formed between the shroud 620 and the collar 634 to ensure turbulent airflow into the distal end 608a of the catheter 608. Likewise, grooves or some other pattern may be formed in the shroud to encourage turbulent airflow. Additionally, a valve member may be included to allow for makeup air in a similar manner as discussed with several of the embodiments above.

Thus there is disclosed an improved respiratory suction apparatus. Those skilled in the art will appreciate numerous modifications which can be made without departing from the scope and spirit of the present invention. The appended claims are intended to cover such modifications.

We claim:

1. A respiratory suction apparatus comprising:
   a suction catheter for removing fluids from a respiratory tract of a patient by insertion of a distal end of the catheter into said respiratory tract and withdrawal of the distal end of the catheter through a portion of said tract while applying negative pressure to a lumen of the catheter;
   a protective sleeve surrounding a proximal longitudinal portion of the catheter;
   a distal adapter configured for communication with a manifold of a patient's artificial airway;
   a collar disposed within the adapter and partially surrounding the distal end of the catheter when the catheter is withdrawn from the manifold, the collar and the catheter defining a substantially uniform cylindrical space around a distal portion of the catheter, the cylindrical space capable of directing lavage solution into the adapter;
   a valve device configured in the adapter to substantially isolate the catheter from the manifold upon withdrawing the distal portion of the suction catheter from said manifold and applying suction through the catheter lumen, said valve device being opened by advancement of said suction catheter through said valve device; and
   a lavage port in fluid communication with the cylindrical space defined by the collar and the catheter, the lavage port in fluid communication with the patient's artificial airway through the cylindrical space and the adapter.

2. A respiratory suction apparatus according to claim 1, wherein the valve device comprises a flap valve disposed distal to a distal end of the collar.

3. A respiratory suction apparatus according to claim 2, wherein the flap valve seats against the distal end of the collar upon applying suction through the catheter lumen.

4. A respiratory suction apparatus according to claim 2, wherein the flap valve seats against a distal end of the catheter upon applying suction through the catheter lumen.

5. A respiratory suction apparatus according to claim 1, further comprising a cleaning enclosure defined within the adapter wherein the distal end of the catheter is exposed to cleaning liquids and turbulent airflow during a cleaning procedure.

6. A respiratory suction apparatus according to claim 5, wherein the valve device is disposed distal to the collar and comprises an aperture therethrough for establishing the turbulent airflow.

7. A respiratory suction apparatus according to claim 6, wherein the valve device is disposed so as to seat against a distal end of the collar.

8. A respiratory suction apparatus according to claim 6, wherein the airflow is filtered ambient air metered through an opening defined through a wall of the cleaning enclosure.

9. A respiratory suction apparatus according to claim 8, further comprising a valve disposed in the opening.

10. A respiratory suction apparatus comprising:
- an elongate suction catheter having a distal end;
- a protective sleeve surrounding a proximal portion of the catheter;
- a distal adapter configured for communication with a manifold of a patient's artificial airway;
- a collar disposed within the adapter and partially surrounding the distal end of the catheter when the catheter is withdrawn from said manifold, the collar and the catheter defining a substantially uniform cylindrical space around a distal portion of the catheter, the cylindrical space capable of directing lavage solution into the adapter;
- a cleaning enclosure defined within the adapter wherein the distal end of the catheter is exposed to cleaning liquids and turbulent airflow during a cleaning procedure;
- means for providing a predetermined rate of airflow to the enclosure responsive to negative pressure within the catheter;
- the catheter being protected at all serviceable times against environmental contamination by a combination of the sleeve, adapter and enclosure;
- a valve device, comprising a flap and a hinge, configured in the adapter whereby the flap occludes the catheter responsive to a pressure differential between said manifold and the enclosure, the catheter opens the flap by manual insertion pressure of the catheter on the flap, and the hinge retains the flap; and
- a lavage port in fluid communication with the cylindrical space defined by the collar and the catheter, the lavage port in fluid communication with the patient's artificial airway through the cylindrical space and the adapter.

11. A respiratory suction apparatus according to claim 10, wherein the rate of airflow is responsive to application of negative pressure in the catheter.

12. A respiratory suction apparatus according to claim 11, wherein the rate of airflow is filtered ambient air and the means for providing a predetermined rate of airflow further comprising an opening in the enclosure.

\* \* \* \* \*